(12) United States Patent
McCutchen (10) Patent No.: US 10,537,840 B2
(45) Date of Patent: Jan. 21, 2020

(54) RADIAL COUNTERFLOW SEPARATION FILTER WITH FOCUSED EXHAUST

(71) Applicant: VORSANA INC., Brush Prairie, WA (US)

(72) Inventor: David J. McCutchen, Portland, OR (US)

(73) Assignee: VORSANA INC., Brush Prairie, WA (US)

( * ) Notice: Subject to any disclaimer, the term of this patent is extended or adjusted under 35 U.S.C. 154(b) by 79 days.

(21) Appl. No.: 15/664,855

(22) Filed: Jul. 31, 2017

(65) Prior Publication Data
US 2019/0030474 A1   Jan. 31, 2019

(51) Int. Cl.
*B01D 19/00* (2006.01)
*B01D 45/14* (2006.01)
(Continued)

(52) U.S. Cl.
CPC ......... *B01D 45/14* (2013.01); *B01D 19/0052* (2013.01); *B01D 19/0057* (2013.01);
(Continued)

(58) Field of Classification Search
CPC .. B01D 45/14; B01D 21/265; B01D 19/0057; C02F 2303/04; C02F 1/4691; C02F 1/02;
(Continued)

(56) References Cited

U.S. PATENT DOCUMENTS

| | | |
|---|---|---|
| 406,968 A | 7/1889 | Tesla |
| 512,340 A | 1/1894 | Tesla |

(Continued)

FOREIGN PATENT DOCUMENTS

| | | |
|---|---|---|
| EP | 0319699 | 6/1989 |
| GB | 2354462 | 3/2001 |

(Continued)

OTHER PUBLICATIONS

King, Tao, "Direct numerical simulation of Open Von Karman Swirling Flow," ScienceDirect, J. Hydrodynamics, 2014, 26(2):166-178.

(Continued)

*Primary Examiner* — Dung H Bui
(74) *Attorney, Agent, or Firm* — Miller Nash Graham & Dunn LLP (57) ABSTRACT

An improved apparatus for filtration has a fluid mixture feed comprising light and heavy fractions fed into the workspace between counter-rotating disk impellers within a tank, thereby forming vortices in the workspace. A static radial exhaust array is located axially in the workspace, comprising exhaust channels, each of which has a peripheral end facing the workspace and an inner end communicating with an axial exhaust drain. An axial pump produces low pressure in the axial exhaust drain, thereby drawing in and anchoring the vortices to the peripheral ends of the exhaust channels so that the exhaust channels can extract the contents of the vortex cores. Vanes can be incorporated into the workspace surface of each disk impeller so that the opposed vanes pass in close proximity, forming vortices along a plurality of radial lanes of intersection, with the peripheral openings of each of the exhaust channels aligned with at least one of the lanes of intersection in the workspace. The feed can be a peripheral feed which enters the workspace radially inward through the periphery of the workspace, or the feed can enter the workspace radially outward through a static axial feed array.

20 Claims, 6 Drawing Sheets

(51) Int. Cl.

| | |
|---|---|
| *B01D 21/26* | (2006.01) |
| *C02F 1/469* | (2006.01) |
| *C12M 1/00* | (2006.01) |
| *C12N 1/12* | (2006.01) |
| *B82Y 30/00* | (2011.01) |
| *C01B 32/162* | (2017.01) |
| *B01J 19/08* | (2006.01) |

(52) U.S. Cl.
CPC ........... B01D 21/265 (2013.01); *B01J 19/088* (2013.01); *B82Y 30/00* (2013.01); *C01B 32/162* (2017.08); *C02F 1/4691* (2013.01); *C02F 2303/04* (2013.01); *C12M 21/02* (2013.01); *C12N 1/12* (2013.01); *H01L 2924/00* (2013.01)

(58) Field of Classification Search
CPC ............ C02F 2201/48; C02F 2209/40; H01L 2924/0002; H01L 2924/00; H01L 23/427; C12M 21/02; C12N 1/12; B82Y 30/00; B82Y 40/00; C01B 32/162; B01J 19/088
See application file for complete search history.

(56) References Cited

U.S. PATENT DOCUMENTS

| | | |
|---|---|---|
| 1,952,281 A | 3/1934 | Ranque |
| 2,422,882 A | 6/1947 | Bramley |
| 2,685,335 A | 8/1954 | McCutchen |
| 2,764,095 A | 9/1956 | Baker |
| 2,867,945 A | 1/1959 | Gotaas et al. |
| 3,187,898 A | 6/1965 | Baker |
| 3,366,564 A | 1/1968 | Allen |
| 3,411,447 A | 11/1968 | Fox |
| 3,464,672 A | 9/1969 | Massa |
| 3,465,187 A | 9/1969 | Breaux |
| 3,468,614 A | 9/1969 | Nilsson |
| 3,491,023 A | 1/1970 | McCormick |
| 3,520,649 A | 7/1970 | Tomany et al. |
| 3,566,610 A | 3/1971 | Fiore |
| 3,603,062 A | 9/1971 | Robbins et al. |
| 3,717,554 A | 2/1973 | Ruthrof |
| 3,731,800 A | 5/1973 | Timson |
| 3,755,644 A | 8/1973 | Lewis |
| 3,769,781 A | 11/1973 | Klein et al. |
| 3,902,876 A | 9/1975 | Moen et al. |
| 3,915,673 A | 10/1975 | Tamai et al. |
| 3,922,871 A | 12/1975 | Bolesta |
| 3,944,865 A | 3/1976 | Jewitt |
| 3,959,923 A | 6/1976 | Selke |
| 3,982,378 A | 9/1976 | Sohre |
| 3,990,631 A | 11/1976 | Schall |
| 3,990,968 A | 11/1976 | Oesterle |
| 3,999,400 A | 12/1976 | Gray |
| 4,037,414 A | 7/1977 | Nicodemus |
| 4,044,943 A | 8/1977 | Brown et al. |
| 4,076,617 A | 2/1978 | Bybel et al. |
| 4,125,439 A | 11/1978 | Fleischmann et al. |
| 4,186,089 A | 1/1980 | Okada |
| 4,201,635 A | 5/1980 | Muller |
| 4,184,084 A | 6/1980 | Crehore |
| 4,272,011 A | 6/1981 | Nagatomo et al. |
| 4,273,562 A | 6/1981 | Niskanen |
| 4,292,051 A | 9/1981 | Kime |
| 4,324,068 A | 4/1982 | Anthony |
| 4,326,666 A | 4/1982 | Fujiwara et al. |
| 4,333,017 A | 6/1982 | O'Connell |
| 4,341,038 A | 7/1982 | Bloch et al. |
| 4,357,152 A | 11/1982 | Duske et al. |
| 4,362,020 A | 12/1982 | Meacher et al. |
| 4,363,540 A | 12/1982 | Strahsner |
| 4,371,382 A | 2/1983 | Ross |
| 4,454,101 A | 6/1984 | Garrison et al. |
| 4,458,153 A | 7/1984 | Wesley |
| 4,479,354 A | 10/1984 | Cosby |
| 4,490,252 A | 12/1984 | Brigante |
| 4,582,513 A | 4/1986 | van der Burgt |
| 4,604,109 A | 8/1986 | Koslow |
| 4,668,383 A | 5/1987 | Watson |
| 4,680,314 A | 7/1987 | Nonomura |
| 4,792,438 A | 12/1988 | Horikoshi |
| 4,832,918 A | 5/1989 | Horikoshi et al. |
| 4,846,780 A | 7/1989 | Galloway et al. |
| 4,925,557 A | 5/1990 | Ahlberg, Jr. et al. |
| 4,957,606 A | 9/1990 | Juvan |
| 4,992,246 A | 2/1991 | Serizawa et al. |
| 4,995,425 A | 2/1991 | Weisenbarger et al. |
| 4,999,597 A | 3/1991 | Gaynor |
| 5,073,262 A | 12/1991 | Ahlberg et al. |
| 5,078,847 A | 1/1992 | Grosman et al. |
| 5,133,190 A | 7/1992 | Abdelmalek |
| 5,137,681 A | 8/1992 | Dougherty |
| 5,143,630 A | 9/1992 | Rolchigo |
| 5,232,726 A | 8/1993 | Clark et al. |
| 5,254,250 A | 10/1993 | Rolchigo et al. |
| 5,275,006 A | 1/1994 | McCutchen |
| 5,368,724 A | 11/1994 | Ayers et al. |
| 5,390,740 A | 2/1995 | Woerheide |
| 5,393,417 A | 2/1995 | Cox |
| 5,393,421 A | 2/1995 | Ohe |
| 5,441,102 A | 8/1995 | Burward-Hoy |
| 5,449,249 A | 9/1995 | Husten |
| 5,451,825 A | 9/1995 | Strohm |
| 5,464,513 A | 11/1995 | Goriachev et al. |
| 5,466,270 A | 11/1995 | Abdelmalek |
| 5,476,537 A | 12/1995 | Yi et al. |
| 5,481,149 A | 1/1996 | Kambe et al. |
| 5,494,585 A | 2/1996 | Cox |
| 5,534,118 A | 7/1996 | McCutchen |
| 5,554,343 A | 9/1996 | Wade |
| 5,578,280 A | 11/1996 | Kazi et al. |
| 5,587,618 A | 12/1996 | Hathaway |
| 5,607,562 A | 3/1997 | Shimamune et al. |
| 5,611,214 A | 3/1997 | Wegeng et al. |
| 5,622,621 A | 4/1997 | Kramer |
| 5,679,249 A | 10/1997 | Fendya et al. |
| 5,688,377 A | 11/1997 | McCutchen |
| 5,725,778 A | 3/1998 | Cho et al. |
| 5,728,186 A | 3/1998 | Jonsson |
| 5,746,789 A | 5/1998 | Wright et al. |
| 5,817,218 A | 10/1998 | Hayashi et al. |
| 5,824,136 A | 10/1998 | Meline |
| 5,851,375 A | 12/1998 | Bodger et al. |
| 5,851,407 A | 12/1998 | Bowman et al. |
| 5,882,530 A | 3/1999 | Chase et al. |
| 5,902,224 A | 5/1999 | Bloom |
| 5,925,324 A | 7/1999 | Greer |
| 5,939,030 A | 8/1999 | Moxley et al. |
| 5,993,674 A | 11/1999 | Rolchigo et al. |
| 6,019,825 A | 2/2000 | Greene et al. |
| 6,037,170 A | 3/2000 | Sekine |
| 6,051,905 A | 4/2000 | Clark |
| 6,106,713 A | 8/2000 | Miller et al. |
| 6,116,027 A | 9/2000 | Smith et al. |
| 6,117,322 A | 9/2000 | Miller et al. |
| 6,149,573 A | 11/2000 | Berger et al. |
| 6,183,714 B1 | 2/2001 | Smalley et al. |
| 6,200,486 B1 | 3/2001 | Chahine et al. |
| 6,203,814 B1 | 3/2001 | Fisher et al. |
| 6,208,512 B1 | 3/2001 | Goldowsky et al. |
| 6,210,575 B1 | 4/2001 | Chase et al. |
| 6,221,260 B1 | 4/2001 | Chahine et al. |
| 6,245,299 B1 | 6/2001 | Shiloh et al. |
| 6,254,764 B1 | 7/2001 | Babington et al. |
| 6,261,525 B1 | 7/2001 | Minace |
| 6,264,898 B1 | 7/2001 | Ingram |
| 6,284,105 B1 | 9/2001 | Eliasson et al. |
| 6,292,085 B1 | 9/2001 | Cho |
| 6,294,139 B1 | 9/2001 | Vicard et al. |
| 6,350,890 B1 | 2/2002 | Kiy et al. |
| 6,376,558 B1 | 4/2002 | Bahner et al. |
| 6,451,175 B1 | 9/2002 | Lal |
| 6,468,499 B1 | 10/2002 | Balachandran et al. |

(56) References Cited

U.S. PATENT DOCUMENTS

| | | | |
|---|---|---|---|
| 6,478,969 B2 | 11/2002 | Brantley et al. | |
| 6,484,503 B1 | 11/2002 | Raz | |
| 6,494,935 B2 | 12/2002 | Cho et al. | |
| 6,495,133 B1 | 12/2002 | Xue | |
| 6,515,391 B2 | 2/2003 | Whitesell | |
| 6,516,617 B1 | 2/2003 | Schwieger | |
| 6,517,612 B1 * | 2/2003 | Crouch | B01D 33/067 95/277 |
| 6,550,531 B1 | 4/2003 | Searls et al. | |
| RE38,130 E | 6/2003 | Adams | |
| 6,603,233 B2 | 8/2003 | Strohm | |
| 6,685,803 B2 | 2/2004 | Lazarovich | |
| 6,716,269 B1 | 4/2004 | Graff | |
| 6,716,335 B2 | 4/2004 | Takesako et al. | |
| H2102 H | 5/2004 | Uhm | |
| 6,737,099 B2 | 5/2004 | Guraya | |
| 6,746,613 B2 | 6/2004 | Korenev | |
| 6,751,940 B1 | 6/2004 | Paul | |
| 6,765,949 B2 | 7/2004 | Chang | |
| 6,774,335 B2 | 8/2004 | Yanobe et al. | |
| 6,777,639 B2 | 8/2004 | Schroder et al. | |
| 6,808,634 B1 | 10/2004 | Zegg | |
| 6,827,820 B1 | 12/2004 | Meinander | |
| 6,856,037 B2 | 2/2005 | Yazawa et al. | |
| 6,872,301 B2 | 3/2005 | Schepis | |
| 6,875,351 B2 | 4/2005 | Arnaud | |
| 6,894,899 B2 | 5/2005 | Wu | |
| 6,916,418 B2 | 7/2005 | Baldasarre et al. | |
| 6,916,425 B2 | 7/2005 | Lotz et al. | |
| 6,923,890 B2 | 8/2005 | Ricatto et al. | |
| 6,924,608 B2 | 8/2005 | Czernichowski et al. | |
| 6,936,228 B2 | 8/2005 | Hirakata et al. | |
| 6,943,461 B2 | 9/2005 | Kaploun | |
| 6,945,314 B2 | 9/2005 | Farrow et al. | |
| 6,966,874 B2 | 11/2005 | Cornay et al. | |
| 6,979,433 B1 | 12/2005 | Saito et al. | |
| 7,002,800 B2 | 2/2006 | Elias et al. | |
| 7,006,605 B1 | 3/2006 | Benavides | |
| 7,008,605 B1 | 3/2006 | Benavides | |
| 7,029,584 B2 | 4/2006 | Blase et al. | |
| 7,033,478 B2 | 4/2006 | Harde | |
| 7,033,481 B1 | 4/2006 | Schlager et al. | |
| 7,035,104 B2 | 4/2006 | Meyer | |
| 7,037,484 B1 | 5/2006 | Brandenburg | |
| 7,041,144 B2 | 5/2006 | Kozyuk | |
| 7,049,724 B2 | 5/2006 | Qu et al. | |
| 7,052,667 B2 | 5/2006 | Loutfy et al. | |
| 7,055,581 B1 | 6/2006 | Roy | |
| 7,056,437 B2 | 6/2006 | Schmid et al. | |
| 7,062,900 B1 | 6/2006 | Brun | |
| 7,094,381 B1 | 8/2006 | Overton et al. | |
| 7,097,676 B2 | 8/2006 | Wootan et al. | |
| 7,121,906 B2 | 10/2006 | Sundel | |
| 7,128,816 B2 | 10/2006 | Denes et al. | |
| 7,150,836 B2 | 12/2006 | Meikrantz | |
| 7,160,426 B2 | 1/2007 | Baosheng | |
| 7,163,637 B2 | 1/2007 | Vannahme et al. | |
| 7,169,305 B2 | 1/2007 | Gomez | |
| 7,174,715 B2 | 2/2007 | Armitage et al. | |
| 7,183,515 B2 | 2/2007 | Miller et al. | |
| 7,217,368 B2 | 5/2007 | Lane | |
| 7,217,638 B2 | 5/2007 | Okawa | |
| 7,238,289 B2 | 7/2007 | Suddath | |
| 7,241,256 B2 | 7/2007 | Cornay et al. | |
| 7,244,360 B2 | 7/2007 | Cho | |
| 7,247,244 B2 | 7/2007 | Kozyuk | |
| 7,262,384 B2 | 8/2007 | Jackson | |
| 7,263,836 B2 | 9/2007 | Gunawardana et al. | |
| 7,264,849 B2 | 9/2007 | Keshner et al. | |
| 7,306,737 B2 | 12/2007 | Langenecker | |
| 7,310,232 B2 | 12/2007 | Touzov | |
| 7,314,516 B2 | 1/2008 | Kozyuk et al. | |
| 7,323,157 B2 | 1/2008 | Kinloch et al. | |
| 7,352,580 B2 | 4/2008 | Tsai | |
| 7,374,685 B2 | 5/2008 | Sun | |
| 7,374,693 B1 | 5/2008 | Routberg et al. | |
| 7,374,731 B2 | 5/2008 | Wang et al. | |
| 7,381,328 B2 | 6/2008 | Schrive et al. | |
| 7,408,186 B2 | 8/2008 | Merkulov et al. | |
| 7,419,603 B2 | 9/2008 | Cho | |
| 7,479,325 B2 | 1/2009 | Fan et al. | |
| 7,757,866 B2 | 7/2010 | McCutchen | |
| 7,771,582 B2 | 8/2010 | Kazem | |
| 7,794,969 B1 | 9/2010 | Reppas et al. | |
| 7,851,211 B2 | 12/2010 | Lu | |
| 7,883,580 B2 | 2/2011 | Barker et al. | |
| 7,901,485 B2 | 3/2011 | McCutchen | |
| 7,980,078 B2 | 7/2011 | McCutchen | |
| 7,987,677 B2 | 8/2011 | McCutchen | |
| 8,025,801 B2 | 9/2011 | McCutchen | |
| 8,268,136 B2 | 9/2012 | McCutchen | |
| 8,474,264 B2 | 7/2013 | McCutchen | |
| 9,611,556 B2 | 4/2017 | McCutchen | |
| 2003/0192831 A1 | 10/2003 | Langenecker | |
| 2004/0007539 A1 | 1/2004 | Denes et al. | |
| 2004/0048364 A1 | 3/2004 | Trosch | |
| 2004/0144314 A1 | 7/2004 | David et al. | |
| 2004/0151654 A1 | 8/2004 | Wei et al. | |
| 2004/0261417 A1 | 12/2004 | Yamashita et al. | |
| 2005/0006801 A1 | 1/2005 | Kinloch | |
| 2005/0118090 A1 | 6/2005 | Shaffer et al. | |
| 2005/0133464 A1 | 6/2005 | Vannahme et al. | |
| 2005/0163696 A1 | 7/2005 | Uhm et al. | |
| 2005/0170089 A1 | 8/2005 | Lashmore et al. | |
| 2006/0010871 A1 | 1/2006 | Frechette et al. | |
| 2006/0057037 A1 | 3/2006 | Anazawa et al. | |
| 2006/0127299 A1 | 6/2006 | Harbec et al. | |
| 2006/0146644 A1 | 7/2006 | Holloway et al. | |
| 2006/0244386 A1 | 11/2006 | Hooke et al. | |
| 2006/0251564 A1 | 11/2006 | Kin et al. | |
| 2007/0001462 A1 | 1/2007 | McNeil | |
| 2007/0045168 A1 | 3/2007 | Levitt et al. | |
| 2007/0048209 A1 | 3/2007 | Smalley et al. | |
| 2007/0048848 A1 | 3/2007 | Sears | |
| 2007/0048859 A1 | 3/2007 | Sears | |
| 2007/0102111 A1 | 5/2007 | Monsma et al. | |
| 2007/0155006 A1 | 7/2007 | Levin | |
| 2007/0163702 A1 | 7/2007 | Sullivan | |
| 2007/0183959 A1 | 8/2007 | Charlier et al. | |
| 2007/0224107 A1 | 9/2007 | Hikata | |
| 2007/0231886 A1 | 10/2007 | Kahlert et al. | |
| 2007/0237959 A1 | 10/2007 | Lemaire | |
| 2008/0023338 A1 | 1/2008 | Stoots et al. | |
| 2008/0086969 A1 | 4/2008 | Taylor | |
| 2008/0170982 A1 | 7/2008 | Zhang et al. | |
| 2009/0013867 A1 | 1/2009 | McCutchen | |
| 2009/0045150 A1 | 2/2009 | McCutchen | |
| 2009/0060827 A1 | 3/2009 | Vinciguerra et al. | |
| 2009/0068727 A1 | 3/2009 | Karr | |
| 2009/0087371 A1 | 4/2009 | Jang et al. | |
| 2009/0113790 A1 | 5/2009 | Erd | |
| 2009/0155864 A1 | 6/2009 | Bauer et al. | |
| 2009/0159461 A1 * | 6/2009 | McCutchen | B01D 9/0022 205/751 |
| 2009/0159523 A1 | 6/2009 | McCutchen | |
| 2009/0200176 A1 | 8/2009 | McCutchen et al. | |
| 2009/0242174 A1 * | 10/2009 | McCutchen | F28D 15/0233 165/104.25 |
| 2009/0246863 A1 | 10/2009 | Lin | |
| 2009/0256175 A1 | 10/2009 | Kim et al. | |
| 2009/0263309 A1 | 10/2009 | McCutchen et al. | |
| 2009/0317901 A1 | 12/2009 | Vance | |
| 2010/0005711 A1 | 1/2010 | McNeff | |
| 2010/0093046 A1 | 4/2010 | Remmereit et al. | |
| 2010/0093074 A1 | 4/2010 | Tooley | |
| 2010/0162620 A1 | 7/2010 | McCaffrey et al. | |
| 2010/0178231 A1 | 7/2010 | Turney et al. | |
| 2010/0190241 A1 | 7/2010 | Jaggi | |
| 2010/0227388 A1 | 9/2010 | Shvabsky et al. | |
| 2010/0255569 A1 | 10/2010 | Camarate de Albuquerque Maranhao | |
| 2010/0273252 A1 | 10/2010 | Lin | |

(56) References Cited

U.S. PATENT DOCUMENTS

2010/0330615 A1 12/2010 Neto
2012/0196336 A1 8/2012 McCutchen

FOREIGN PATENT DOCUMENTS

WO 2008007750 1/2008
WO 2009142765 11/2009

OTHER PUBLICATIONS

"All Biochar is Not Created Equally"; http://www.biocharsolutions.com/technology.html; printed on Feb. 13, 2012.
Chen, C. et al., Cultivation, photobioreactor design and harvesting of microalgae for biodiesel production: A critical review; Bioresource Technology 102 (2011) 71-81.
"Biochar Pathways for Different Environments"; International Biochar Initiative, Aug. 26, 2009, pp. 1-2.
Mata, T. et al., Microalgae for biodiesel production and other applications: A review; Renewable and Sustainable Energy Reviews 14 (2010) 217-232.
Park, W. et al., Determination of Pyrolysis Temperature for Charring Materials; National Institute of Standards and Technology, U.S. Dept. of Commerce, NIST GCR-07-913, Dec. 2007.
Sheehan, J. et al., A Look Back at the U.S. Department of Energy's Aquatic Species Program—Biodiesel from Algae; National Renewable Energy Laboratory, NREL/TP-580-24190, Jul. 1998.
Shelef, G. et al., "Microalgae Harvesting and Processing" A Literature Review; U.S. Department of Energy, Technion Research and Development Foundation Ltd.; SERI/STR-231-2396, Aug. 1984.
Ugwu, C. U. et al., "Photobioreactors for mass cultivation of algae"; Bioresource Technology 99 (2008) 4021-4028.
Zellwerk GmbH, "Cells Working for You"; retrieved at http://www.glenmills.com/index-z_rp.shtml; printed on Dec. 29, 2010.
"Algaewheel Brochure", retrieved at http://www.algaewheel.com (2012).
Bergles, A. (May 2001). "The Implications and Challenges of Enhanced Heat Transfer for the Chemical Process Industries". Institution of Chemical Engineers, Trans IChemE, vol. 79, Part A, pp. 437-444.
Feeley, T. et al. (Jul. 2005). "Department of Energy/Office of Fossil Energy's Power Plant Water Management R&D Program". DOE/FE's Power Plant Water Management R&D Program Summary, pp. 1-14.
Gao, C. (2005). "Experimental Study on the Ranque-Hilsch Vortex Tube". CIP-Data Library Technische Universiteit Eindhoven, pp. 1-148.
Hellyar, K. (1979). "Gas Liquefaction Using a Ranque-Hilsch Vortex Teube: Design Criteria and Bibliography". Massachusetts Institute of Technology, pp. 1-68.
Promvonge, P. et al. (2005). "Investigation on the Vortex Thermal Separation in a Vortex Tube Refrigerator". ScienceAsia 31, pp. 215-223.
Ottino, J.M., Mixing, Chaotic Advection, and Turbulence, Annu. Rev. Fluid Mech. 1990, 22: pp. 207-253.
UOP LLC (2003). "FCC Vortex Separation Technology: The VDS Design and VSS Design". Process Technology and Equipment (4 pages).
Kronenberg, Klaus J., "Experimental Evidence for Effects of Magnetic Fields on Moving Water," IEEE Transactions on Magnetics, vol. Mag-21, No. 5, Sep. 1985.
Lee, Sangho, et al., "Control of Scale Formation in Reverse Osmosis by Membrane Rotation," Desalination 155 (2003) pp. 131-139, p. 137.
Ahmed, et al., "Feasibility of Salt Production from Inland RO Desalination Plant Reject Brine: A Case Study," Desalination 158 (2003) pp. 109-117.
De La Torre et al., Slow Dynamics in a Turbulent von Karman Swirling Flow, arXiv:physics/0702151v1, Feb. 19, 2007.4 pgs.
Raterman et al., A Vortex Contactor for Carbon Dioxide Separations, www.net1.doe.gov/publications/proceedings/01/carbon_seq/7b3.pdf (date unknown), 11 pgs.
Crocker et al., Experimental Results of a Vortex Tube Air Separator For Advanced Space Transportation, AIAA 2003-4451, 39th Joint Propulsion Conference & Exhibit, Huntsville, Alabama, Jul. 20-23, 2003, pp. 1-12.
IPCC Special Report on Carbon Dioxide Capture and Storage, Chapter 3, Capture of CO2 (2005), pp. 108-122, 168-171.
US EPA, External Combustion Sources, Bituminous and Sub-bituminous Coal Combustion, Sep. 1998, 15 pgs.
Secondment to the International Test Centre for CO2 Capture (ITC), University of Regina, Canada; Jan.-Mar. 2005, Report No. COAL R303 DTI/Pub URN 06/798, May 2005, pp. 1-94.
Ivan Delbende et al., Various Aspects of Fluid Vortices, C.R. Mechanique 332 (2004) pp. 767-781.
Daviaud et al., Turbulence in Rotating Flows, 2005, http://www-drecam.cea.fr/spec/Pres/Git/TRF/trf.htm, 2 pgs.
Lopez, J.M., Characteristics of Endwall and Sidewall Boundary Layers in a Rotating Cylinder With a Differentially Rotating Endwall, J. Fluid Mech. (1998), vol. 359, pp. 49-79.
Bockris, J., et al., "On the Splitting of Water," Int. J. Hydrogen Energy, vol. 10, No. 30, pp. 179-201, 1985, Bergamon Press Ltd., Great Britain.
Hawkes, G., et al., INL/CON-06-11720 Preprint, "Three Dimensional CFD Model of a Planar Solid Oxide Electrolysis Cell for Co-Electrolysis of Steam and Carbon Dioxide," Nov. 2006, Idaho National Laboratory, Idaho, US, including 2 pg. INL flyer entitled Syntrolysis.
Indarto, A., "Kinetic of CO2 Reduction by Gliding Arc Plasma," Asian Journal of Water, Environment and Pollution, vol. 4, No. 1, pp. 191-194, Oct. 9, 2006.
Koziol, K, et al., "High-Performance Carbon Nantube Fiber," Science, vol. 318, pp. 1892-1895, Dec. 21, 2007.
Lee, S.J., et al., "Large scale synthesis of carbon nanotubes by plasma rotating arc discharge technique," Diamond and Related Materials 11, pp. 914-917, 2002, Elsevier Science B.V.
Perlmutter, Comparison of Gypsum Dewatering Technologies at Flue Gas Desulfurization Plants, Presented at the 45th ISA Power Industry Division (POWID) Conference San Diego, California Jun. 2-7, 2002, 9 pgs.
Tarrer, Development of a New Gravity Sedimentation Process for Dewatering Flue Gas Cleaning Wastes, EPA-600/S7-84-084, Sep. 1984, 5 pgs.
Bellucci et al., "Study of Field Emission of Multi-Walled C Nanotubes Synthesized by Arc Discharge", J. Phys: Condens. Matter 19 (2007) 395014 (7pp.), retrieved Mar. 20, 2009 from the Internet: URL<http://www.iop.org/EJ/abstract/0953-8984/19/39/395014>, Abstract.
Keider, et al., "On the Conditions of Carbon Nanotube Growth in the Arc Discharge," Nanotechnology vol. 15 Issue 11, Oct. 1, 2004, pp. 1571-1575.
Nojeh, A., et al., "Electric-Field-Directed Growth of Carbon Nanotubes in Two Dimensions", Journal of Vacuum Science & Technology B, vol. 22 Issue 6, 2004, pp. 3421-3425, American Vacuum Society.
Oon, C.H., et al., "In Situ nanowire growth for electrical interconnects", Nanotechnology, 2004,vol. 15 No. 5, pp. 687-691.
Britt, Robert Roy, "The Worlds Smallest Motor," Apr. 12, 2005, retrieved at http://www.livescience.com/6969-world-smallest-motor.html.
Kalra, C.S. et al., "Gliding arc in tornado using a reverse vortex flow," Review of Scientific Instruments 76, 025110, pp. 1-7, Jan. 21, 2005, American Institute of Physics.
Hinkov, S., et al., "Optical Plasma Control During Arc Carbon Nanotube Growth" 2001, Proceedings of the Sixth Applied Diamond Conference/Second Frontier Carbon Technology Joint Conference (ADC/FCT 2001).
Chen, J. et al., "Fractal-like free networks Increasing the permeability," Physical Review E 75, 056301 (2007) pp. 1-8.
Zandbergen, P., Dijkstra D., "Von Karman Swirling Flows," Annual Reviews Fluid Mech. (1987), 19:465-491.
Hnatiuc, E. et al., "Cold Plasma Electrochemical Reactor with Rotary Discharge," retrieved at http://www.ut.ee/hakone8/papers/T6/Hnatiuc1(TP).pdf, Jul. 31, 2003, pp. 181-198.

(56) References Cited

OTHER PUBLICATIONS

Czernichowski, A., "GlidArc Assisted Preparation of the Synthesis Gas from Natural and Waste Hydrocarbons Gases," Oil & Gas Science Technology-Rev. IFP, vol. 56 No. 2 (2001), pp. 181-198.
Tesla, N., "Notes on a Unipolar Dynamo," The Electrical Engineer, Sep. 2, 1891, pp. 23-26.
Young, I., et al., "Physical Water Treatment for the Mitigation of Mineral Fouling in Cooling-Tower Water Applications," 2003 ECI Conference on Heat Exchanger Fouling and Cleaning: Fundamental Applications (2004), pp. 20-31.
Kronenberg, K, "Experimental Evidence for Effects of Magnetic Fields on Moving Water," IEEE Transactions on Magnetics, vol. MAG-21, No. 5, Sep. 1985 pp. 2059-2061.
Lebovka, N., Vorobiev, E., "The kinetics of inactivation of spheroidal microbial cells by pulsed electric fields," arXiv 3704.2750v1, Apr. 20, 2007, pp. 1-22.
Khachatryan, A., et al., "Graphite-to-diamond transformation induced by ultrasound cavitation," Diamond & Related Materials 17 (2008), pp. 931-936.
Van Der Walt, E., Grundingh, M., "The use of UV in combination with physical unit processes for treatment of raw water in small or rural communities," retreived at www.svargo-us.org, Nov. 18, 2007, pp. 1-6.
Neff, R., "Applying magneto-hydrodynamic physics to water purification," IBM Innovation to Be Greener Competition, The National Society of High school Scholars, Apr. 30, 2008, pp. 1-7.
Flannigan, D. et al., "Sonochemistry and sonoluminescense in ionic liquids, molten salts, and concentrated electrolyte solutions," Journal of Organometallic Chemistry 690 (2005), pp. 3513-3517.
UOP, "FCC Vortex Separation Technology: the VDS (TM) Design," retrieved at www.uop.com (2003) pp. 1-3.
Konno, A., et al., "Observation of cavitation bubble collapse by high-speed video," retrieved at www.fluid.mech.kogakuin.ac.jp, Dec. 11, 2003, pp. 1-6.
Rosa, E., "Cavitation pressure of water," http://matdl.org/repository/list.php?cat=quick_filter&search_keys%5B0%5D=cavitation+pressure (2007), pp. 1-3.
Leszcynska, D., Ahmad H., "Toxic elements in soil and groundwater: Short-term study on electrokinetic removal of arsenic in the presense of other ions," International Journal of Environmental Research and Public Health (2006), pp. 196-201.
Kim, S., et al., "Seed crystalization with cavitation for enhanced removal of calcium in water," J. Ind. Eng. Chem, vol. 13, No. 1 (2007), pp. 79-83.
Loske, A., et al., "Bactericidal effect of underwater shock waves," retrieved at http://www.sea-acustica.es/Sevilla02/utt01012, Sep. 2002, pp. 1-5.
Daniels, D., "Put a lid on rising chemical costs," Power, Sep. 15, 2008. pp. 1-9.
Gupta, S., "Investigation of a physical disinfection process based on pulsed underwater corona discharges," retrieved at FZKA 7336 digbib.ubka.uni-karlsruhe.de/volitexte/documetns/23373.pdf, Sep. 2007, pp. 1-135.
Shtern, V., Hussain, F., "Collapse, Symmetry, Breaking and Hysteresis in Swirling Flows," Annu. Rev. Fluid Mech. (1999) 31:537-566.
Lu et al., "A Technique for the Manufacture of Long Hollow Diamond Fibers by Chemical Vapor Deposition", Journal of Materials Science Letters, 14, 1995, pp. 1448-1450.
Koziol et al., "High-Performance Carbon Nanotube Fiber", Science Express, 10.1261147635, Nov. 15, 2007, pp. 1-6.
Koziol et al., Cambridgenanotube1147635s1.mpg (identified as "Movie S1" in Koziol et al., High-Performance Carbon Nanotube Fiber, Science Express, 10.1261147635, Nov. 15, 2007, pp. 1-6.), CD-R, IBM-PC, MS Windows, 2.22 MB.

* cited by examiner

Fig. 11
Radial counterflow in the workspace

RADIAL COUNTERFLOW SEPARATION FILTER WITH FOCUSED EXHAUST

BACKGROUND

Several designs have been described for the separation of fluid mixtures using organized turbulent effects between counter-rotating disks to create a vortex network. These include the Wilmot H. McCutchen U.S. Pat. No. 7,901,485 (Mar. 8, 2011) "Radial Counterflow Carbon Capture and Flue Gas Scrubbing", U.S. Pat. No. 8,025,801 (Sep. 27, 2011)"Radial Counterflow Inductive Desalination", U.S. Pat. No. 7,987,677 (Aug. 2, 2011) and U.S. Pat. No. 8,474,264 (Jul. 2, 2013) "Radial Counterflow Steam Stripper", U.S. Pat. No. 9,611,556 (Apr. 4, 2017) "Radial Counterflow Shear Electrolysis", and "Radial Counterflow Reactor with Applied Radiant Energy" U.S. patent application Ser. No. 13/360,564 by Wilmot H. McCutchen and the Applicant.

These all describe the formation of a vortex network in a shear layer. As shown in Tao Xing, "Direct numerical simulation of Open von Karman Swirling Flow" from the Journal of Hydrodynamics 2014, 26(2):165-177, this network includes opposing spiral networks of vortices near each rotating disk, plus complex and changing vortices in the shear layer between them.

The cited patents describe the separation of lighter fractions in a fluid mixture, with the lighter fractions sucked inward through the cores of the vortices while the heavier fractions are centrifuged outward from the cores and toward the periphery of the disks. The separation effect is tied to the rotation speed of the vortex, which is controlled by the vortex size. If suction to the core is applied to concentrate the vortex, then the g forces increases, in the manner of a skater drawing in their arms to create a faster spin, with the higher g's increasing the separation of the fractions by weight.

A baffle is also described in the cited patents for separating the inward and outward flows from the workspace between the disks. All of these have been shown as solid disks in structure. These baffles do not include means for a direct connection to the vortices in the workspace to act as a drain or exhaust for the just the cores of the vortices, so an axial drain may tend to draw in all of the components of the workspace without discrimination.

SUMMARY

An improved apparatus for filtration has a fluid mixture feed comprising light and heavy fractions, fed into a tank, with at least one pair of disk impellers within the tank, arranged roughly in parallel and defining a workspace between them, capable of coaxial counter-rotation as the feed enters the workspace, thereby forming vortices in the fluid mixture in the workspace. One or more motors are coupled to the disk impellers to produce the counter-rotation. A static radial exhaust array is located axially in the workspace between the disk impellers and approximately centered on the axis of rotation. The exhaust array comprises channels, each of which has a peripheral end facing the workspace and an inner end communicating with an axial exhaust drain. An axial pump produces low pressure in the axial exhaust drain, thereby drawing in the vortices in the workspace so that a plurality of vortex ends are anchored to the peripheral ends of the exhaust channels.

Vanes can be incorporated into the workspace surface of each disk impeller, arranged in a non-radial fashion, so that as the disk impellers counter-rotate and the opposed vanes pass in close proximity, the passing vanes will form vortices in the workspace along a plurality of radial lanes of intersection. The peripheral openings of each of the exhaust channels are aligned with at least one of the lanes of intersection in the workspace, thereby anchoring and increasing the performance of the vortices found there. The fluid mixture can be advected toward the axis or away from the axis, depending on the direction of rotation of the disk and the angle of the vane relative to an orthogonal line from the axis of rotation. The angle of the vane can vary relative to the distance from the axis to change the direction of advection relative to the axis of rotation. The vanes can be in a branching design to allow more lanes of intersection to be formed, and more exhaust channels can be added to be aligned to these extra lanes.

The peripheral ends of the exhaust channels can be incorporated as peripheral openings in a continuous approximately disk shaped structure, with the inner axial ends of the exhaust channels coupled to a hollow interior which is in communication with the axial exhaust drain.

The feed can be a peripheral feed which enters the workspace radially inward through the periphery of the workspace, or the feed can enter the workspace radially outward through a static axial feed array.

The axial feed array has at least one axial feed pipe and a plurality of peripheral openings located between the peripheral openings of the exhaust array.

A peripheral feed into the workspace can be a uniform feed from the tank, or it can be done through at least one peripheral feed pipe which is coupled to a static feed array with a plurality of peripheral openings located between the peripheral openings of the exhaust array.

The feed array peripheral openings can be located closer to the axis of rotation relative to the exhaust array peripheral openings, or be located farther from the axis of rotation. The feed array peripheral openings can be coplanar with the exhaust array peripheral openings, or they can be located above the plane of the exhaust array peripheral openings, or below them, or both above and below them, or coplanar and also above and below them. Both the feed array and the exhaust array can be incorporated into a continuous static structure.

The peripheral exhaust openings can be made in a conical shape to focus on the vortex cores. The exhaust channels can be tilted at an angle relative to a radial line drawn orthogonally from the axis of rotation, in order to produce an exhaust vortex into the axial exhaust drain.

LISTED PARTS

1. Enclosing tank
2. Upper disk
3. Lower disk
4. Peripheral end of exhaust channel
5. Lower disk vanes
6. Inner end of exhaust channel
7. Upper disk vanes
8. Workspace
9. Rotation for upper disk
10. Rotation for lower disk
11. Region of vortices in workspace
12. Vortex end
13. Lane of intersection
15. Exhaust array
17. Exhaust channel
18. Angle of exhaust channel
19. Axial exhaust drain
21. Feed channel
23. Axial feed pipe
25. Main feed channel
27. Axis of rotation
29. Peripheral feed pipe
31. Upper peripheral feed channel
33. Coplanar peripheral feed channel
35. Lower peripheral feed channel
37. Exhaust pump
39. Feed pump
41. Lower rotation drive
43. Upper rotation drive
45. Vortex reflector
47. Vortex core
49. Branch on vane
51. Additional lane of intersection
53. Additional exhaust channel aligned to additional lane
55. Feed through boundary layer
57. Flow through vortex core
59. Inward flowing vortex
61. Outward flowing vortex
63. Overall flow to periphery
65. Conical surface on inside of exhaust channel
67. Conical surface on outside of exhaust channel
69. Exhaust vortex
71. Static central pipe
73. Metal reflector
75. Induction coil
77. Peripheral drive
79. Peripheral drive wheel
81. Shear layer
83. Boundary layer

DETAILED DESCRIPTION

This disclosure describes an improved method of extracting the light fractions from the vortex cores in a radial counterflow regime.

Figure 1:
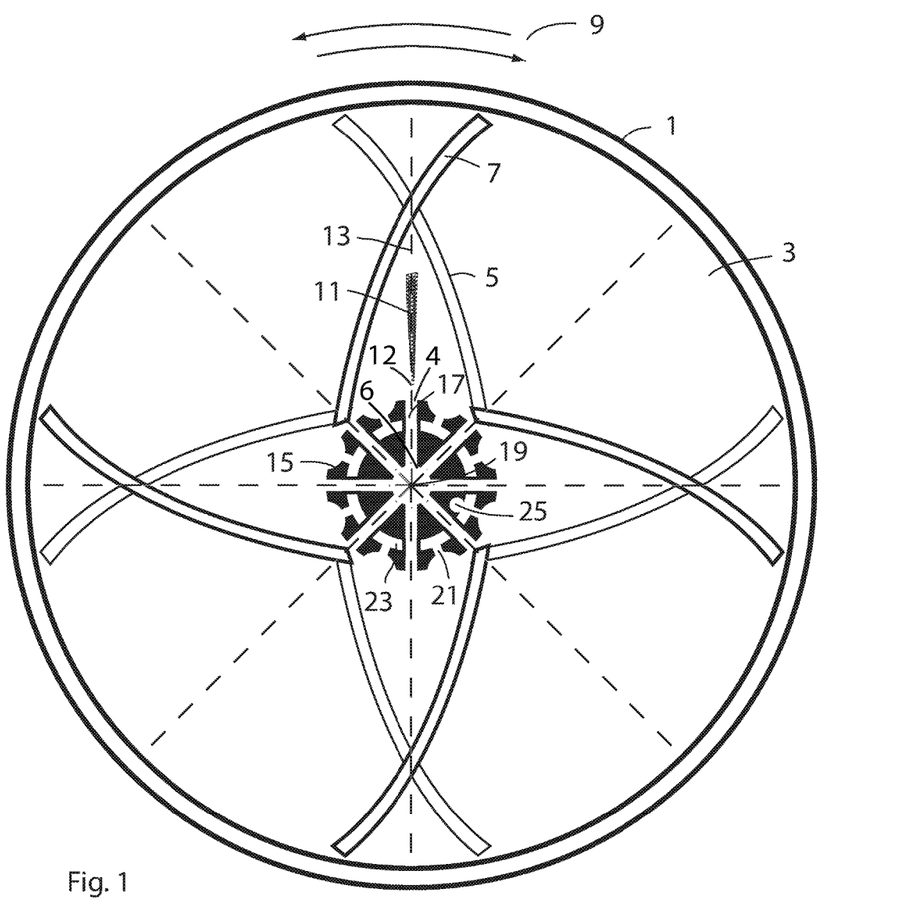
FIG. 1—A top view cross section of the workspace between two counter-rotating disks in a tank.

FIG. 1 shows a top view cross section of the workspace 8 between two counter-rotating disk impellers, or disks, in a tank 1, with the bottom disk visible at 3. The counter-rotation of the disk impellers will create a network of vortices in the workspace, shown as 8 in FIG. 2, either from the motion of the disk surfaces alone, or with the assistance of structures such as textured surfaces, or protruding vanes. A vane coupled to the bottom disk is shown at 5, and a vane coupled to the top disk is shown at 7. As the vanes pass nearby each other from counter-rotation 9, 10 of the disks, vortices 11 will tend to form along the radial lanes of intersection 13. A static axial exhaust array 15 includes a plurality of exhaust channels 17, each aligned with one of these lanes of intersection for sucking out the cores of the vortices. The exhaust array and feed array could be implemented as a continuous disk shaped, or continuous static structure. These exhaust channels each have a peripheral end 4 facing toward the workspace, and an inner end 6, leading to an axial exhaust drain 19. A plurality of feed channels 21 to allow a fluid mixture feed to enter the workspace between the lanes of intersection 13 can be fed by an axial feed pipe 23 and a main feed line 25.

Figure 2:
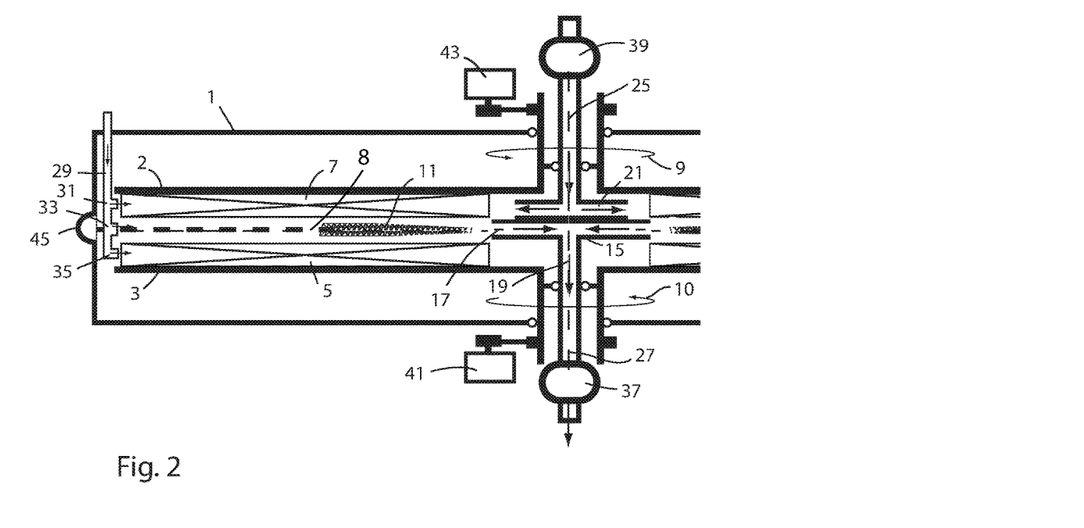
FIG. 2—A partial cross section of the tank enclosing the top disk and the bottom disk.

FIG. 2 shows a partial cross section of the tank 1 enclosing the top disk 2 and the bottom disk 3. Vanes on the bottom disk 5 and the top disk, as they pass in close proximity during counter-rotation 9, will tend to form vortices 11 along the lanes of intersection. The lane of intersection region of vortex activity will also be denoted as a dashed line in these drawings. Each lane of intersection is aligned to an exhaust channel 17 in an axial exhaust array 15 which leads to an axial exhaust drain 19 approximately centered on the axis of rotation 27. Feed channels 21 fed by a main feed line 25 and axial feed pipes 23, making up the feed array, can introduce the feed into the workspace, especially between the lanes of intersection, where the feed flow will interfere less with the vortex formation. Here the feed channel 21 is shown above the exhaust channel, and for simplicity, shown as coplanar in this cross section, although as shown in FIG. 1, this would not actually be the case. The feed channels, besides being between the exhaust channels, could be located above or below them, or both above and below, or coplanar with the exhaust channels, as well as above and below them. The feed channels can be axial, or from the periphery of the workspace, such as from a peripheral feed line 29, leading to upper peripheral feed channels 31, coplanar peripheral feed channels 33, and lower peripheral feed channels 35 relative to the plane of the exhaust channels. An exhaust pump 37 on the axial exhaust drain 19 causes low pressure in the exhaust channels 17 to attract the vortices to be fixed by their ends 12 shown in FIG. 1 to the peripheral ends 4 of the exhaust channels. A feed pump 39 is used to introduce the feed through the feed channels. Motors and drive means for the bottom disk 41 and the top disk 43 produce counter-rotation in the disks centered on the axis of rotation 27, while the feed and exhaust assemblies remain static, and can be implemented as a continuous static structure such as 15. A curved vortex reflector 45 in the tank wall aligned to a lane of intersection will help to make the vortices cores rebound inward and improve the flow through the exhaust channels.

Figure 3:
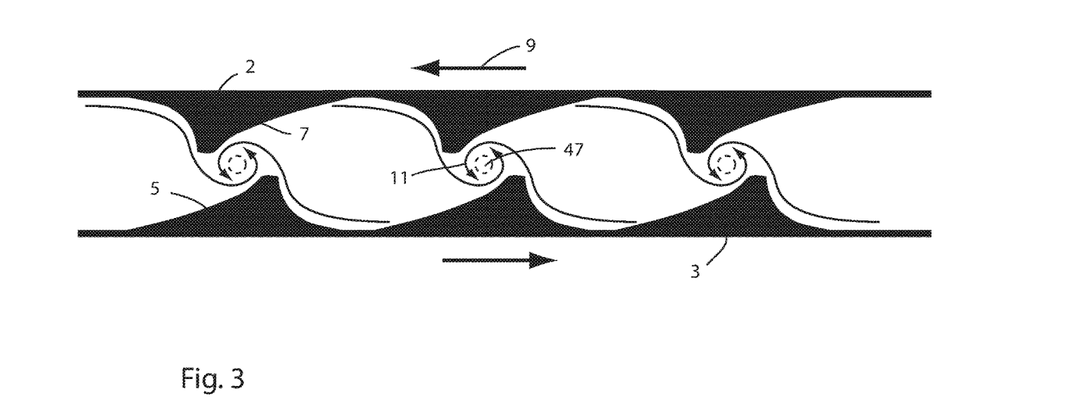
FIG. 3—A cylindrical cross section of the workspace, looking outward from the center, showing passing vanes and the turbulence patterns they would generate.

FIG. 3 is a cylindrical cross section of the workspace, looking outward from the center, showing passing vanes and the turbulence patterns they would generate. At their lanes of intersection, the mechanical forcing of the fluid motion from the vanes 5, 7 will tend to form vortices 11 in the fluid mixture, whose cores 47 are the focus of the exhaust channels. The vane profile should be designed to maximize this effect.

Figure 4:
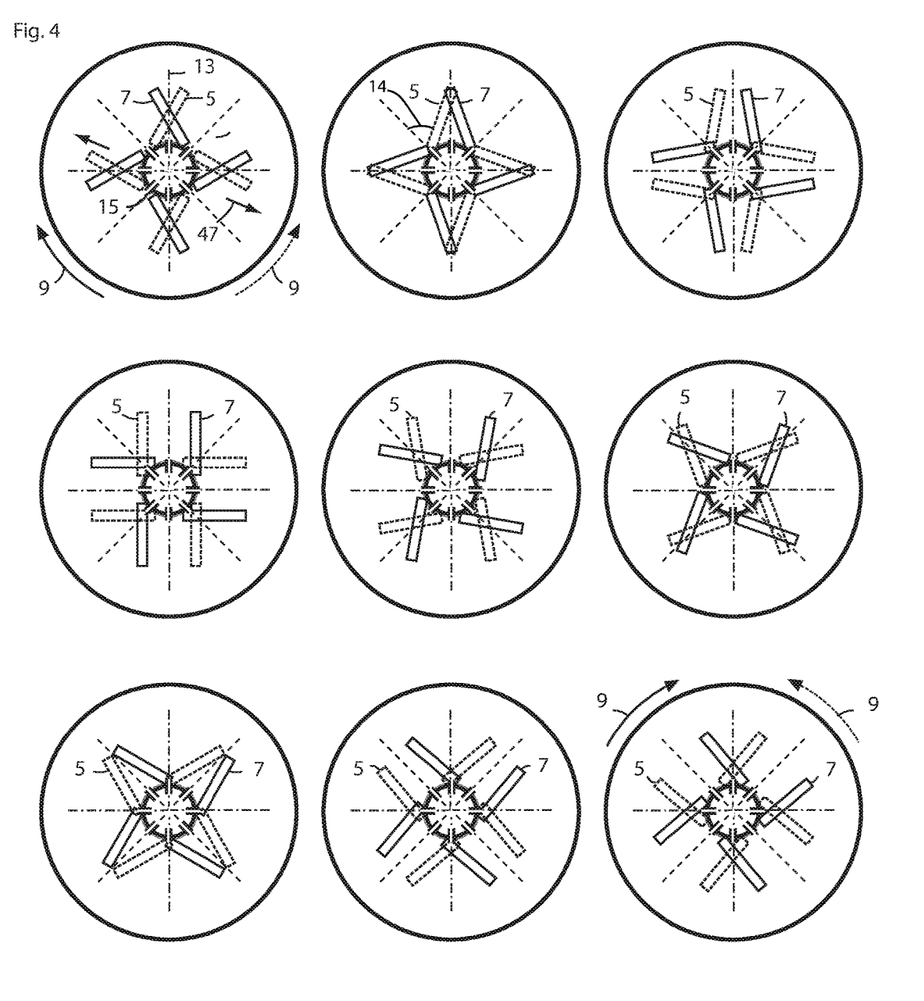
FIG. 4—A top cross section of the workspace with the vanes from the bottom disk and the top disk shown, forming radial lanes of intersection which are the focus of the exhaust array.

FIG. 4 is a top cross section of the workspace in the manner of FIG. 1, with the vanes from the bottom disk 5 and the top disk 7 shown, forming radial lanes of intersection 13 which are the focus of the exhaust array 15. The intersection of the vanes and how they form these radial lanes is shown here by multiple successive rotations of ten degrees each. The direction of rotation of the disk 9 together with the angle of the vanes such as 14 relative to the lane of intersection combine to advect the fluid mixture, in this case in an advection direction outward 47.

Figure 5:
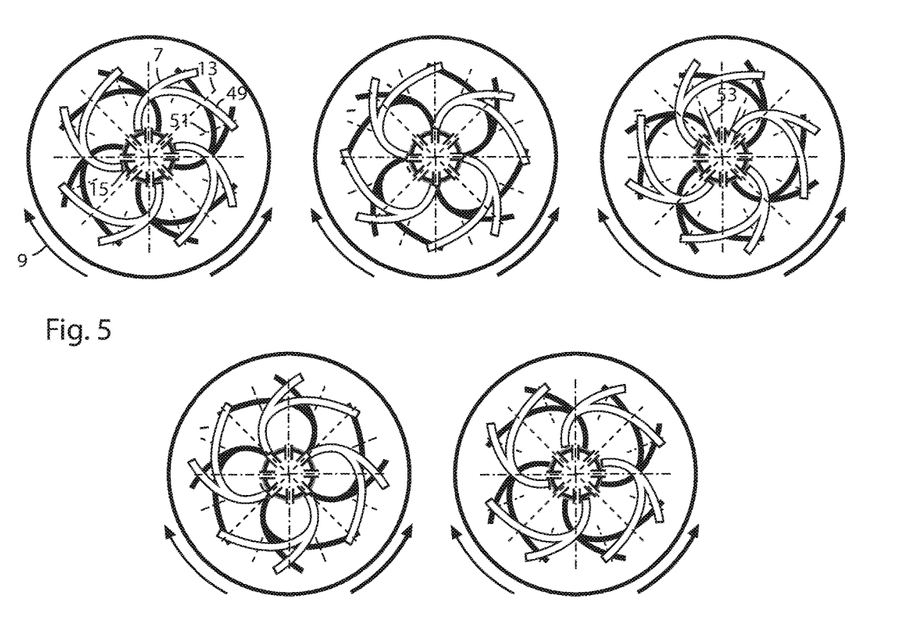
FIG. 5—A top cross section that shows the effect of a branching design for the vanes, wherein an added vane branch produces added lanes of intersection between the original lanes of intersection.

FIG. 5 is also a top cross section that shows the effect of a branching design for the vanes, wherein an added vane branch 49 produces added lanes of intersection 51 between the original lanes of intersection 13. The counter-rotation 9, 10 of the top and bottom vanes is shown in 22.5 degree increments. These added lanes of intersection 51 can be aligned to added exhaust channels 53 added to the axial exhaust assembly 15.

Figure 6:
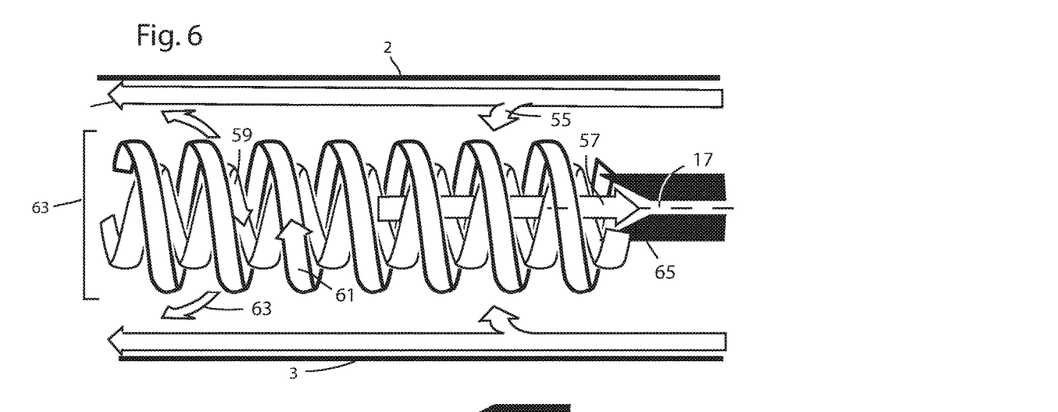
FIG. 6—A cross section of a summary of the vortex patterns in the workspace, together with an exhaust channel.

FIG. 6 is a cross section of a detail of the patterns of the vortex layer 11 in the workspace, together with an exhaust channel 17. Between disks 2 and 3, the feed can enter the workspace from a boundary layer 55. In the workspace, the mechanically forced vortices, especially in the lanes of intersection, will tend to have lighter fractions at their core while heavier fractions are centrifugated outward. The vortex core 57 will be drawn into the exhaust channel 17 by low pressure, as part of an inwardly moving inner vortex 59, surrounded by an outer vortex 61 moving outwardly toward the periphery, as part of a general outward flow 63 of the rejected heavier fractions. The exhaust channel 17 shown here has a conical inner section 65 which concentrates and accelerates the vortex flow going into the channel, thereby increasing the centrifugal rejection of the heavier fractions.

Figure 7:
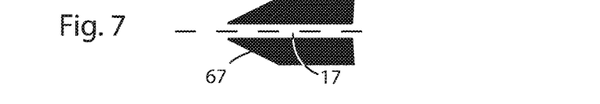
FIG. 7—An alternate configuration for the design of an exhaust channel 17 with a conical outer portion FIG. 8—A cross section of the exhaust assembly showing angled exhaust channels which help create a central exhaust vortex for the most efficient exhaust flow.

FIG. 7 shows an alternate configuration for the design of an exhaust channel 17 with a conical outer portion 67 to help to strip away and reject the outer layers of the overall vortex.

Figure 8:
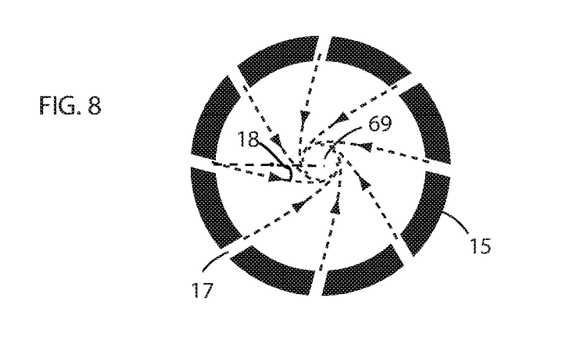

FIG. 8 is a cross section of the exhaust assembly 15 showing angled exhaust channels 17, having an angle 18 from what would be a straight exhaust channel, which help create a central exhaust vortex 69 for the most efficient exhaust flow.

Figure 9:
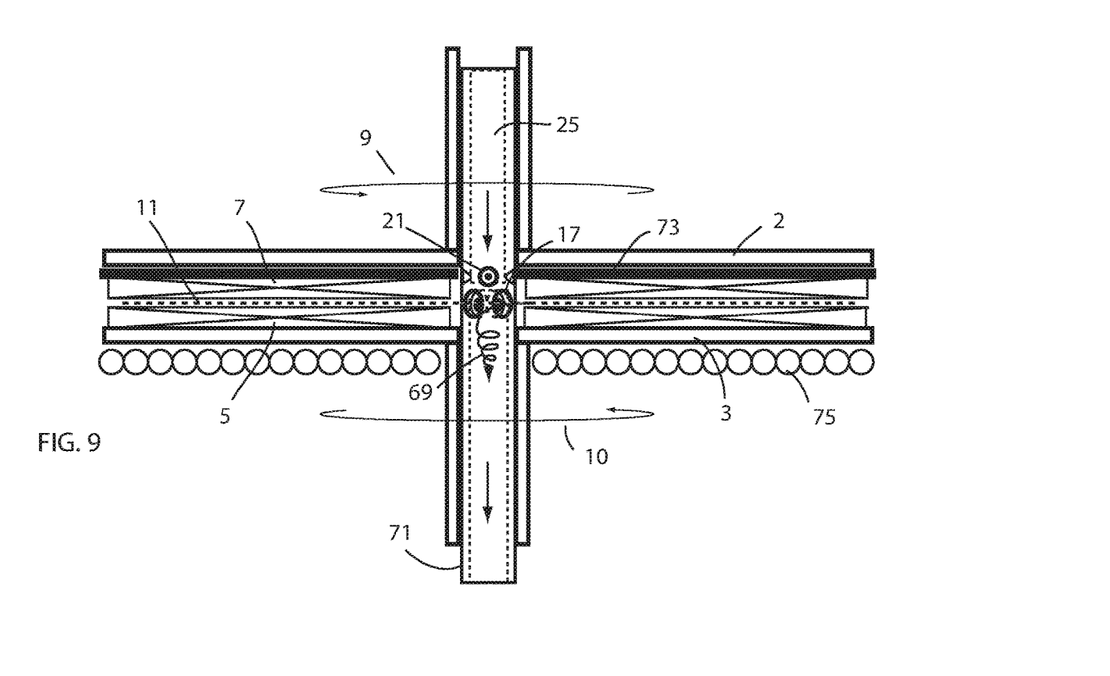
FIG. 9—A cross section of an electromechanical reactor.

FIG. 9 shows a cross section of an electromechanical reactor according to the present disclosure, combined with the description in the previously cited U.S. Pat. No. 8,025,801. The disks 2, 3 each have vanes 5,7 and are counter-rotated 9,10 to produce a vortex layer 11 leading to exhaust channels 17, which in this case are angled conical angled holes to produce an exhaust vortex 69 in a static central pipe 71. This central pipe is divided vertically here into an upper feed section and a lower exhaust section. The upper feed section has a feed channel 25 leading to feed channels 21, which in this case also have a conical design. This design is for an electromagnetic desalinator, with a static radio frequency induction coil 73 combined with a metal electromagnetic reflection layer 75. These elements create differential motion in the salts and electrolytes in brine while leaving pure water unaffected, to aid in the separation and extraction of the water.

Figure 10:
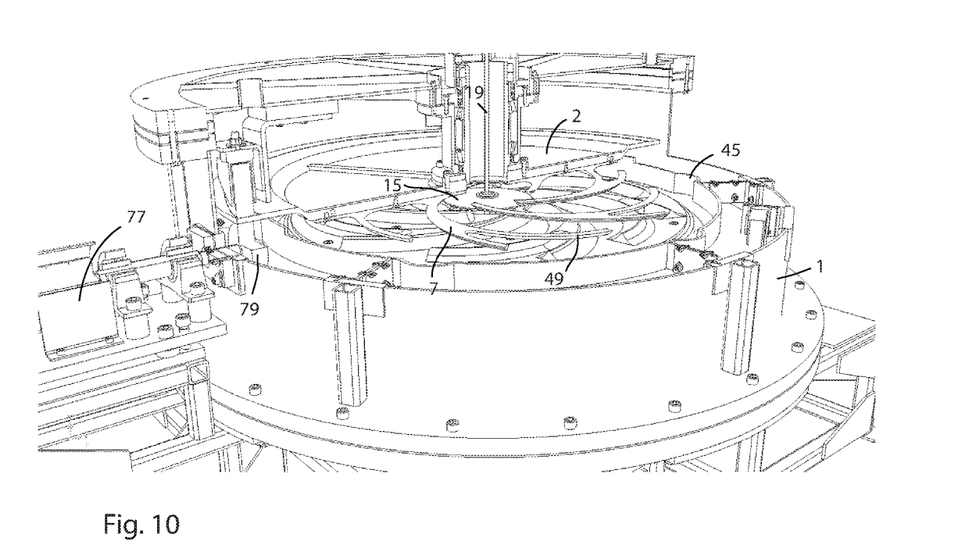
FIG. 10—A partial cross section of a machine design incorporating elements of this description.

FIG. 10 shows a partial cross section of a machine design incorporating elements of this description. The tank 1 encloses the disks, such as the top disk 2. The axial exhaust assembly 15 and axial exhaust drain 19 are between the two counter-rotating sets of vanes, such as the top vane 7, which also has a branch 49. A vortex reflector 45 is at the edge of the workspace to help reflect the cores of the vortices back toward the axis. A single peripheral drive motor 77 is used here, with a peripheral drive wheel 79 which contacts the top and bottom disks simultaneously, driving them in counter-rotation at the same time as the wheel turns.

Figure 11:
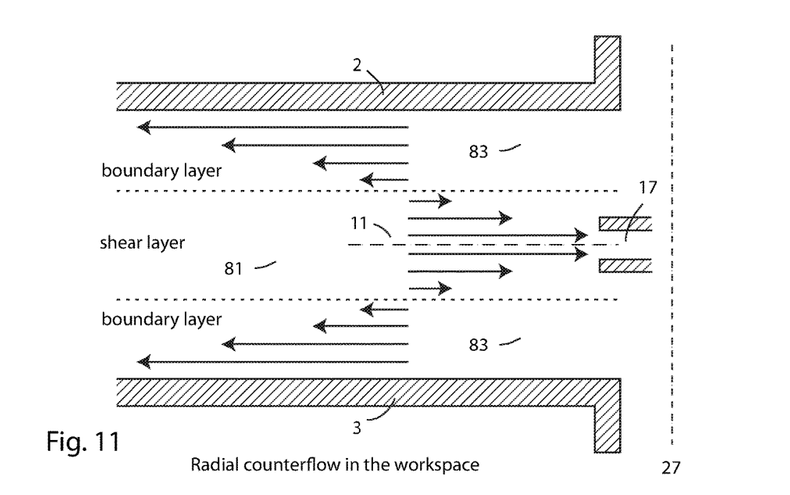
FIG. 11—A simplified overview of radial counterflow in the workspace.

FIG. 11 shows a simplified overview of radial counterflow in the workspace, bounded by the disks 2,3 showing motion vectors for the flow of the components in the shear layer 81 between the boundary layers 83, and an axial exhaust channel 17 near the axis of rotation 27.

Ramifications and Scope

The separation profile of the disks can different than the parallel disks shown here. For one example of a variable disk profile, the disks can flare toward the periphery to form a much wider gap there than near the axis. Any vanes would also conform to the flared disk profile. This can allow for a different type of vortex formation process in the workspace, with a wider and slower vortex at the edge leading to a faster and narrower vortex toward the center. The variable disk profile can also be reversed, with a wider disk separation toward the center than at the periphery.

The vanes described can be built into the disk surfaces or be attached as separate parts. The angle of the vanes can be varied from the examples shown here. For example, if a C-shaped vane were centered on a line of intersection, the vane's rotation could serve to first advect the feed outward from the axis of rotation, then slow the outward advection down to a standstill, and then advect it inward from the region nearer to the periphery. Another alternative is an S-shaped vane. The control of the rate of outward or inward advections allows for the optimal control of residence time and feed flow for the vortex separation processing.

The low pressure in the exhaust channels can be produced also by pressurizing the tank and the workspace relative to the lower pressure in the axial exhaust.

If the feed is pressurized enough to turn the impellers by acting on the vanes, as described in the previously cited U.S. Pat. Nos. 7,987,677 and 8,474,264, then a drive motor to turn the disks would not be necessary, and the mechanical work from the rotation of the disks could be used to turn a generator to produce power.

The fluid mixture feed can be gaseous, such as a flue gas feed with soot and other heavy fraction pollutants mixed with fresh air, or be liquid, such as a brine or water with sediment. It can also be a mix of the two, such as steam with entrained water droplets, or liquid with gaseous bubbles, especially the kind that emerge from the liquid with low pressure. Slurries can also be used, with the liquid extracted through the exhaust channels. This extraction mechanism can also be used for separation of fractions with differing viscosity, with the lighter viscosity fractions concentrating in the vortex cores. It can also be used for high temperature applications, such as the separation of molten components in a furnace.

The rejected heavy fractions that exit the workspace into the tank are then disposed of by suitable means, while the extracted light fractions are used separately. Multiple devices can be used in a chain, such as by having the light fractions from one stage used as the feed in another stage. The design of each stage can be different depending on the nature of the feed, such as having a sediment extraction stage followed by a brine desalination stage.

The parts should be made of a suitable material for the application to be used. For example, refractory materials would be used for the separation of molten materials, while corrosion resistant components would be used for a corrosive feed. All of the components should be designed for durability and easy maintenance.

While the embodiments of the present invention have been particularly shown and described above, it will be understood by one of ordinary skill in the art that various changes in form and details may be made therein without departing from the spirit and scope of the present invention as defined by the following claims.

The invention claimed is:

1. An apparatus for filtration comprising:
a fluid mixture feed comprising light and heavy fractions, fed into a tank;
at least one pair of disk impellers within the tank, arranged in parallel and defining a workspace between them, the disk impellers capable of coaxial counter-rotation as the feed enters the workspace to form vortices in the fluid mixture in the workspace;
one or more motors coupled to the disk impellers to produce said counter-rotation;
a static radial exhaust array located axially in the workspace between the disk impellers and approximately centered on an axis of rotation of the disk impellers, said static radial exhaust array comprising a plurality of exhaust channels, each channel having a peripheral end facing the workspace and an inner end communicating with an axial exhaust drain; and
an exhaust pump to produce low pressure in the axial exhaust drain to draw the vortices into the workspace so that a plurality of vortex ends is anchored to the peripheral ends of the plurality of exhaust channels.

2. The apparatus of claim 1, further comprising vanes incorporated into the workspace surface of each disk impeller, arranged in a non-radial fashion so that, as the disk impellers counter-rotate and the opposed vanes pass in close proximity, the passing vanes will form vortices in the workspace along a plurality of radial lanes of intersection, and the peripheral ends of each of the exhaust channels are aligned with at least one of the lanes of intersection in the workspace to anchor and increase the performance of the vortices.

3. The apparatus of claim 2, wherein the fluid mixture is advected toward the axis of rotation or away from the axis of rotation, depending on the direction of rotation of the disk impellers and an angle of the vane relative to an orthogonal line from the axis of rotation.

4. The apparatus of claim 3, wherein the angle of the vane varies relative to the distance from the axis of rotation to change the direction of advection relative to the axis of rotation.

5. The apparatus of claim 1, wherein the peripheral ends of the exhaust channels are incorporated as peripheral openings in a continuous disk shaped structure with the inner ends of the exhaust channels coupled to a hollow interior in communication with the axial exhaust drain.

6. The apparatus of claim 1, further comprising a static axial feed array having at least one axial feed pipe and a plurality of feed channels.

7. The apparatus of claim 6, wherein the feed channels are coplanar with the exhaust array peripheral ends.

8. The apparatus of claim 6, wherein the feed channels are located above the plane of the exhaust array peripheral ends.

9. The apparatus of claim 6, wherein the feed channels are located below the plane of the exhaust array peripheral ends.

10. The apparatus of claim 6, wherein the feed channels are located both above and below the plane of the exhaust array peripheral ends.

11. The apparatus of claim 6, wherein the feed channels are coplanar and also located both above and below the plane of the exhaust array peripheral ends.

12. The apparatus of claim 6, wherein both the static axial feed array and the exhaust array are incorporated into a continuous static structure.

13. The apparatus of claim 1, wherein the fluid mixture feed is a peripheral feed which enters the workspace radially inward through the periphery of the workspace.

14. The apparatus of claim 13, wherein the peripheral feed into the workspace is a uniform feed from the tank.

15. The apparatus of claim 13, wherein the peripheral feed into the workspace is done through at least one peripheral feed pipe coupled to a static axial feed array comprising a plurality of feed channels located between the peripheral ends of the exhaust array.

16. The apparatus of claim 6, wherein the static axial feed array has at least one axial feed pipe and a plurality of feed channels located between the peripheral ends of the exhaust array.

17. The apparatus of claim 16, wherein the feed channels are located closer to the axis of rotation relative to the exhaust array peripheral ends.

18. The apparatus of claim 16, wherein the feed channels are located farther from the axis of rotation relative to the exhaust array peripheral ends.

19. The apparatus of claim 1, wherein the peripheral exhaust ends are in a conical shape to focus on the vortex cores.

20. The apparatus of claim 1, wherein the exhaust channels are tilted at an angle relative to a radial line drawn orthogonally from the axis of rotation, in order to produce an exhaust vortex into the axial exhaust drain.

* * * * *